United States Patent [19]
Szoka, Jr. et al.

[11] Patent Number: 5,972,600
[45] Date of Patent: Oct. 26, 1999

[54] SEPARATION OF ACTIVE COMPLEXES

[75] Inventors: Francis C. Szoka, Jr.; Yuhong Xu; Jinkang Wang, all of San Francisco, Calif.

[73] Assignee: The Regents of the University of California, Oakland, Calif.

[21] Appl. No.: 08/482,110

[22] Filed: Jun. 7, 1995

Related U.S. Application Data

[63] Continuation-in-part of application No. 08/092,200, Jul. 14, 1993, abandoned, and application No. 07/913,669, Jul. 14, 1992, abandoned, which is a continuation-in-part of application No. 07/864,876, Apr. 3, 1992, abandoned.

[51] Int. Cl.$^6$ ...................................................... C12Q 1/68
[52] U.S. Cl. ................................................ 435/6; 435/458
[58] Field of Search .............................. 435/172.3, 6, 458

[56] References Cited

PUBLICATIONS

Deshayes et al. EMBO Journal. vol. 4, No. 11, pp. 2731–2737, 1985.
Faust et al. Virology. vol. 168, pp. 128–137, 1989.
Kawano et al. Experimental Cell Research. vol. 161, pp. 460–472, 1985.
Shimizu et al. J. Biochem. vol. 98, pp. 1473–1485, 1985.
Witkiewicz et al. Febs Letters. vol. 90, No. 2, pp. 313–317, 1978.
Gershon et al. Mode of Formation and Structural Features of DNA–Cationic Liposome Complexes Used for Transfection. Biochemistry. 32: 7143–7151, 1993.
Alberts et al. Fractionation of Cell Contents in Molecular Biology of the Cell, 2nd edn., Garland Publishing, Inc., New York, 1989, pp. 163–165.

Primary Examiner—Nancy Degen
Assistant Examiner—Irem Yucel
Attorney, Agent, or Firm—Nathan P. Koenig; Crosby, Heafey, Roach & May

[57] ABSTRACT

The invention separates defined, active complexes by a characteristic from Defined, active complexes that share a particular physicochemical characteristic such as density, surface charge or particle size are separated from complexes formed by the association of a polynucleotide with a transfecting component that increases transfection activity, such as a lipid, cationic lipid, liposome, peptide, cationic peptide, dendrimer or polycation. In a preferred embodiment, polynucleotide-transfecting component complexes are ultracentrifuged to resolve one or more bands corresponding to complexes having a specific polynucleotide-transfecting component interaction. Polynucleotide complexes having a cationic liposome transfecting component resolve into two primary bands corresponding to complexes formed either under excess lipid conditions or under excess polynucleotide conditions. In an alternate embodiment, polynucleotide-transfecting component complexes are resolved using cross-flow electrophoresis to identify complexes having specific interactions and to separate them from excess initial components.

17 Claims, 8 Drawing Sheets

FIG. 2

DISTRIBUTION PROFILES OF CATIONIC LIPOSOME/DNA MIXTURES AFTER SUCROSE GRADIENT ULTRA CENTRIFUGATION:

| MIXING CHARGE RATIO (LIPID/DNA) | FREE LIPOSOME (2%) | BAND I (10%) (POSITIVELY CHARGED COMPLEXES) | MINOR BANDS | BAND II (17%) (NEGATIVELY CHARGED COMPLEXES) | FREE DNA (>25%) |
|---|---|---|---|---|---|
| 10/1 | ++ | ++ | | | |
| 5/1 | + | ++ | | | |
| 2/1 | | ++ | TRACE | | |
| 1/1 | PERCIPITATION | | | | |
| 1/2 | | | | ++ | + |
| 1/5 | | | | ++ | ++ |

FIG. 5
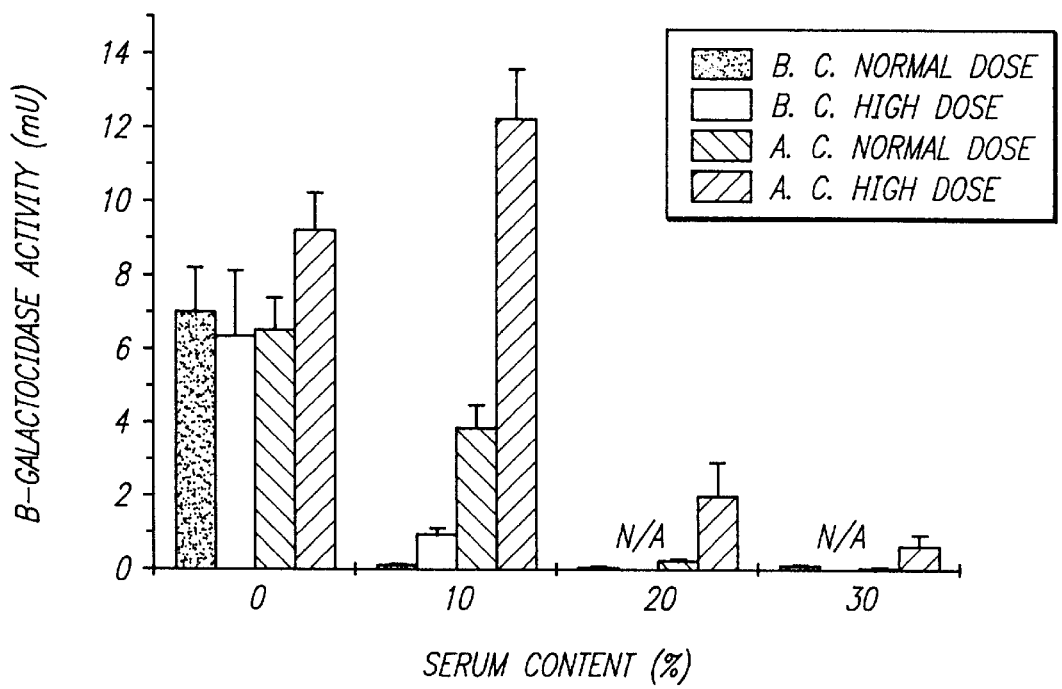
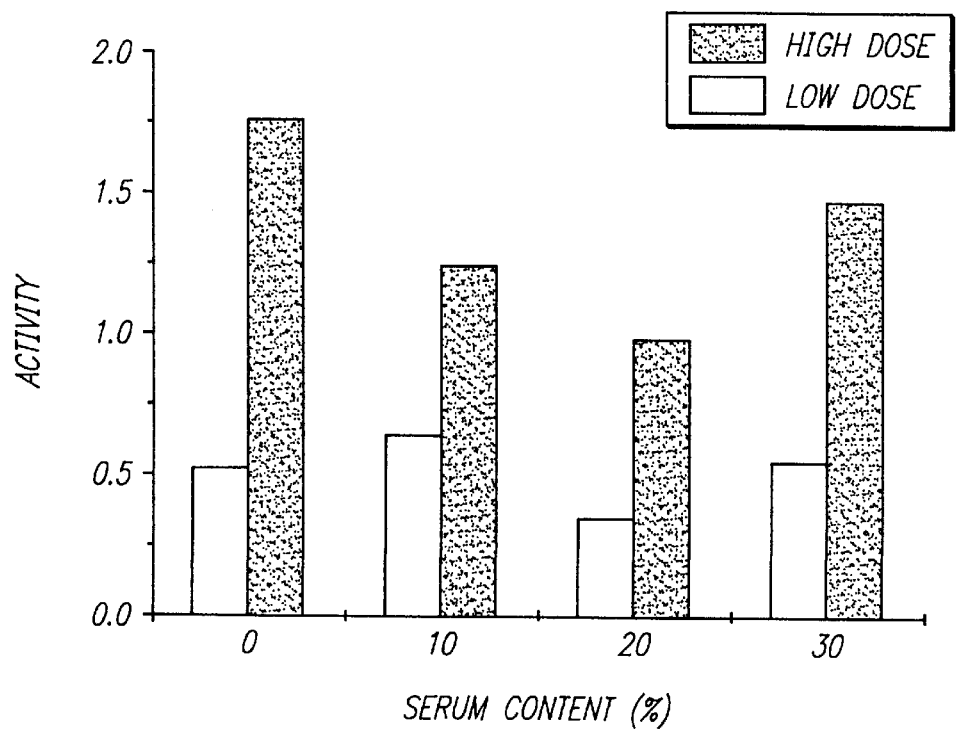
FIG. 6

SPERMINE-5-CARBOXYGLYCINE (N'-STEARYL - N'-OLEYL) AMIDE TETRATRIFLUOROACETIC ACID SALT (JK-75)

SPERMINE-5-CARBOXYGLYCINE (N'-STEARYL- N'-ELAIDYL) AMIDE TETRATRIFLUOROACETIC ACID SALT (JK-76)

AGMATINYL CARBOXYCHOLESTEROL ACETIC ACID SALT (AG-Chol)

SPERMINE-5-CARBOXY-β-ALANINE CHOLESTERYL ESTER
TETRATRIFLUOROACETIC ACID SALT (CAS)

2,6-DIAMINOHEXANOEYL β-ALANINE CHOLESTERYL ESTER
BISTRIFLUOROACETIC ACID SALT (CAL)

FIG. 12
2,4-DIAMINOBUTYROYL β-ALANINE CHOLESTERYL ESTER BISTRIFLUOROACETIC ACID SALT (CAB)
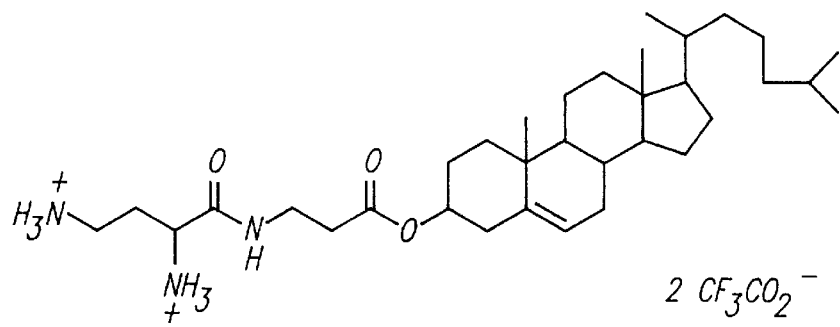
N,N-Bis(3-AMINOPROPYL)-3-AMINOPROPIONYL β-ALANINE CHOLESTERYL ESTER TRISTRIFLUOROACETIC ACID SALT (CASD)
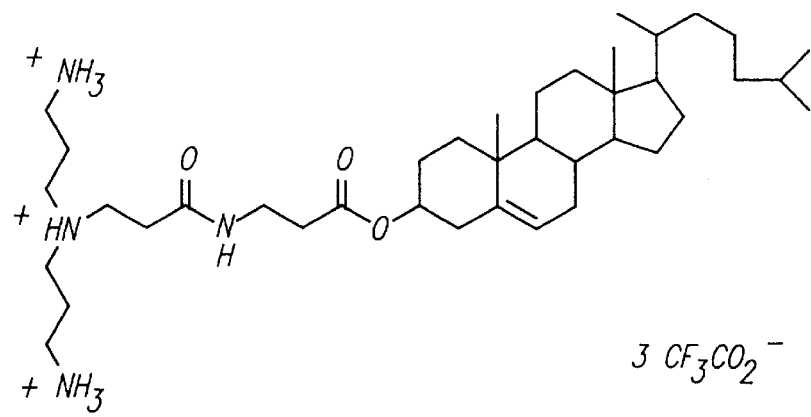
FIG. 13
[N, N-Bis(2-HYDROXYETHYL)-2-AMINOETHYL]AMINOCARBOXY CHOLESTERYL ESTER (JK-154)
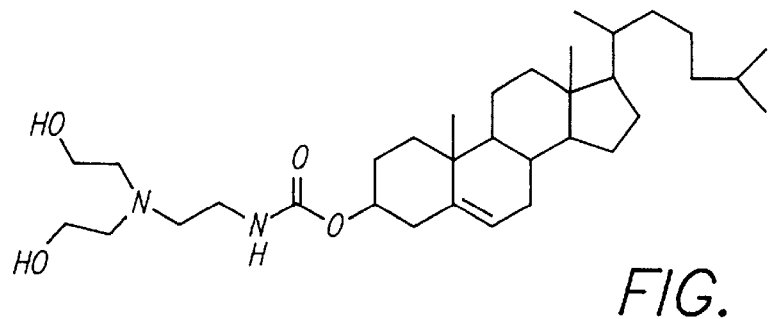
FIG. 14

CARNITINE ESTER LIPIDS
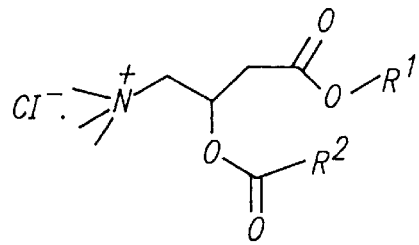
FIG. 15
$R^1 = (CH_2)_n CH_3$ n=2 TO 30, 1 TO 6 UNSATURATED BONDS OR ISO $CH_3$ GROUPS
STEARYL STEAROYL CARNITINE ESTER CHLORIDE SALT (SSCE) FIG. 16
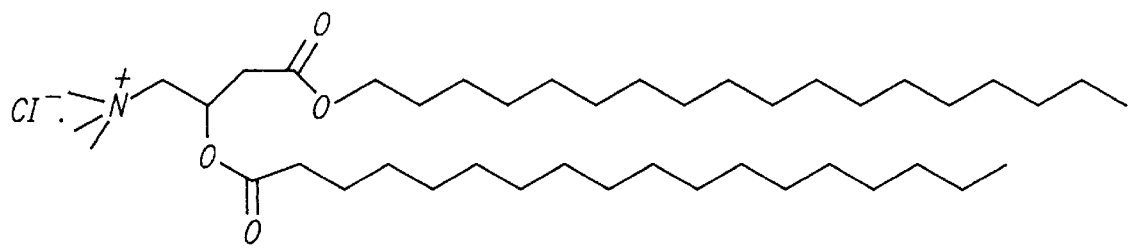
STEARYL OLEOYL CARNITINE ESTER CHLORIDE (SOCE) FIG. 17
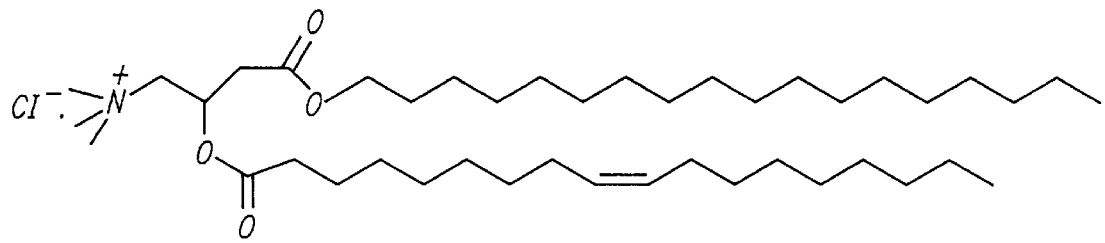
PALMITYL PALMITOYL CARNITINE ESTER CHLORIDE (PPCE) FIG. 18
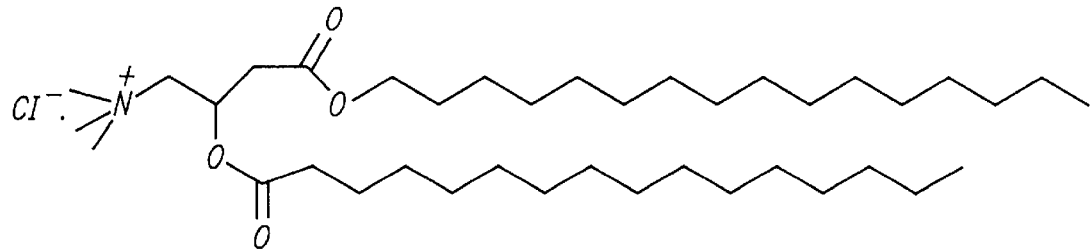
MYRISTYL MYRISTOYL CARNITINE ESTER CHLORIDE (MMCE) FIG. 19
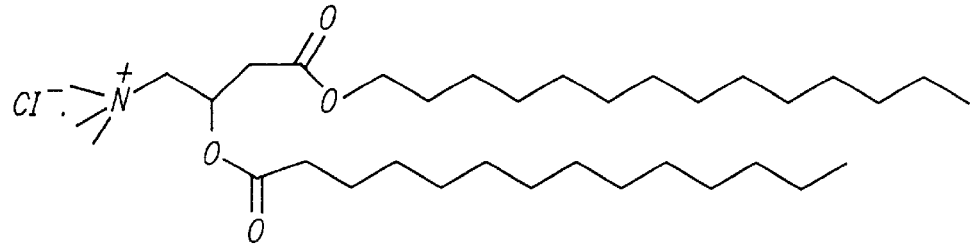

SEPARATION OF ACTIVE COMPLEXES

RELATION TO OTHER APPLICATIONS

This application is a continuation-in-part of U.S. application Ser. No. 08/092,200 filed Jul. 14, 1993, now abandoned, and U.S. application Ser. No. 07/913,669 filed Jul. 14, 1992, now abandoned, which is a continuation-in-part of U.S. application Ser. No. 07/864,876 filed Apr. 3, 1992, now abandoned.

ACKNOWLEDGMENT OF GOVERNMENT SUPPORT

The government has rights in this invention pursuant to Grant No. GM-30163 awarded by the National Institutes of Health.

BACKGROUND ART

Molecular biologists have identified the chromosomal defects in a large number of human hereditary diseases, raising the prospects for cures using gene therapy. This emerging branch of medicine aims to correct genetic defects by transferring cloned and functionally active genes into the afflicted cells. Several systems and polymers suitable for the delivery of polynucleotides are known in the art. In addition, gene therapy may be useful to deliver therapeutic genes to treat various acquired and infectious diseases, autoimmune diseases and cancer.

Polycations such as polylysine and DEAE-dextran promote the uptake of proteins and single- and double-stranded polynucleotides into animal cells. Polylysines help assemble DNA into a compact structure, destabilize cell membranes, and provide a handle for the attachment of other effectors to the nucleic acid. The neutralization and condensation of DNA by polylysines into small (ca 100 nm) toroid-like structures, promotes the endocytosis of the nucleic acid into cells in vitro. The endocytic process may be further stimulated by the covalent attachment to the polycation of specific ligands like transferrin, asialoorosomucoid or insulin.

Other useful polynucleotide complexes involve masking the polynucleotide to prevent degradation. Microparticulates, such as erythrocyte ghosts, reconstituted viral envelopes and liposomes have been used in part as protection in gene transfer. One successful liposome system uses the cationic lipid n-[1-(2,3-dioleyloxy)propyl]-N,N,N-trimethylammonium chloride [DOTMA], mixed with phosphatidylethanolamine [PE] to form the reagent Lipofectin™. Substitutes for DOTMA including lipopolyamine, lipophilic polylysines, and a cationic cholesterol have been used to mediate gene transfer in culture. Other useful lipids include 2,3-dioleyloxy-N-[2-(sperminecarboxyamido)ethyl]-N,N-dimethyl-1-propanaminium trifluoroacetate [DOSPA], [DOTAP], [DOGG], dimethyldioctadecylammonium bromide [DDAB], cetyldimethylethylammonium bromide [CDAB], cetyltrimethylethylammonium bromide [CTAB], dioctadecyidimethylammonium bromide [DDMB], DL-stearyl stearoyl carnitine ester [DL-SSCE], L-stearyl stearoyl carnitine ester [L-SSCE], DL-stearyl oleoyl carnitine ester [DL-SOCE], DL-palmityl palmitoyl carnitine ester [DL-PPCE], DL-myristyl myristoyl carnitine ester [DL-MMCE], L-myristyl myristoyl carnitine ester [L-MMCE], dioleoylphosphatidylcholine [DOPC], monooleoyl-glycerol [MOG], and cholesterol [Chol]. A difficulty associated with polynucleotide-liposome complexes is that depending on the ratio of the two components, the concentration of the components, and the ionic conditions while mixing, the complexes formed vary greatly in size, in electrostatic properties, in lipid and polynucleotide composition and in ability to interact with biological systems.

Gene transfer efficiency may also be improved by targeting the polynucleotide to the cell of choice. Various procedures based upon receptor mediated endocytosis have recently been described for gene transfer. A cell-specific ligand-polylysine complex was bound to nucleic acids through charge interactions, and the resulting complex was taken up efficiently by the target cells, such as in the case of the human hepatoma cell line HepG2 and of rat hepatocytes in vivo using this delivery system with asialoorosomucoid as a ligand. The stable expression of an enzymatic activity in HepG2 cells following insulin-directed targeting as well as the transferrin-polycation-mediated delivery of a plasmid into the human leukemic cell line K-562 and the subsequent expression of the encoded luciferase gene, have been reported. However, the described delivery systems require the linking of high molecular weight targeting proteins to polynucleotides through a polylysine linker. These large ligand-polycation conjugates also are heterogenous in size and composition, chemically ill-defined, and difficult to prepare in a reproducible fashion.

The use of polycations to neutralize the polynucleotide charge aids the permeabilization of the membrane and the translocation of the polynucleotide. Cationic lipids have also been used for this purpose. Certain cationic lipids termed lipopolyamines and lipointercalants are also known.

Transfection efficiency may also be increased when the polynucleotide is associated with various peptides. Certain useful amphipathic peptides assume α-helix or β-pleated sheet secondary structures, presenting a charged face and a neutral face. Cationic proteins increase transfection by condensing the polynucleotide.

Other polycations have been shown to promote transfection when associated with polynucleotides. Complexes formed with dendrimers, bulky three-dimensional polymers built by reiterative reaction sequences around a core molecule that may be prepared in varied molecular weights and sizes, efficiently transfer polynucleotides. Other three-dimensional, branched polycations are also useful.

Specific examples of useful self-assembling polynucleotide delivery systems may be found in U.S. patent applications Ser. No. 08/092,200, filed Jul. 14, 1992, and Ser. No. 07/913,669, filed Jul. 14, 1993, which are hereby incorporated in their entirety by reference thereto.

Despite the usefulness of polynucleotide delivery systems, the polynucleotide conjugates can be heterogenous in size and composition, chemically ill-defined, and difficult to prepare in a reproducible fashion. Further, the compound associated with the polynucleotide often is cytotoxic. This greatly limits the concentration at which the complexes can be delivered. Accordingly, there remains a need for means to select desirable polynucleotide complexes and to maximize the permissible concentration of delivered polynucleotide. The present invention satisfies this and other needs.

SUMMARY OF THE INVENTION

The invention separates defined, active complexes by a physicochemical characteristic from complexes formed by the association of a polynucleotide associated with a transfecting component that increases transfection activity, such as a lipid, cationic lipid, liposome, peptide, cationic peptide, dendrimer or polycation. Active complexes that share a particular characteristic such as density, surface charge or particle size are separated from the excess mixing components. In a preferred embodiment, polynucleotide-transfecting component complexes are ultracentrifuged to resolve one or more bands corresponding to complexes having a specific polynucleotide-transfecting component interaction. When the transfecting component comprises a cationic liposome, gradient processed complexes will resolve into two primary bands corresponding to complexes formed either under excess lipid conditions or under excess polynucleotide conditions. The resolution of the complexes is substantially independent of initial charge ratio. Analysis of average particle size and zeta potential indicate the specific complexes share physical properties and therefore likely correspond to specific polynucleotide-transfecting component interactions.

In an alternate embodiment, polynucleotide-transfecting component complexes are resolved using cross-flow electrophoresis to identify complexes having specific interactions and to separate them from excess initial components.

The invention also comprises active polynucleotide-transfecting component complexes separated by the above methods. The active complexes exhibit greater transfective activity than equal doses of the unresolved complexes. Such complexes are used to deliver genetic information to target cells either in vivo or in vitro.

BRIEF DESCRIPTION OF THE DRAWINGS

FIG. 2 shows the distribution profiles of gradient processed polynucleotide-liposome complexes at various charge ratios.

FIG. 5 shows in vitro transfection activity of gradient processed, positively charged polynucleotide-liposome complexes at various serum concentrations.

FIG. 6 shows in vitro transfection activity of gradient processed, negatively charged polynucleotide-liposome complexes at various serum concentrations.

FIGS. 7–19 show transfecting components comprising particular cationic lipids.

DETAILED DESCRIPTION OF THE INVENTION

Figure 1:
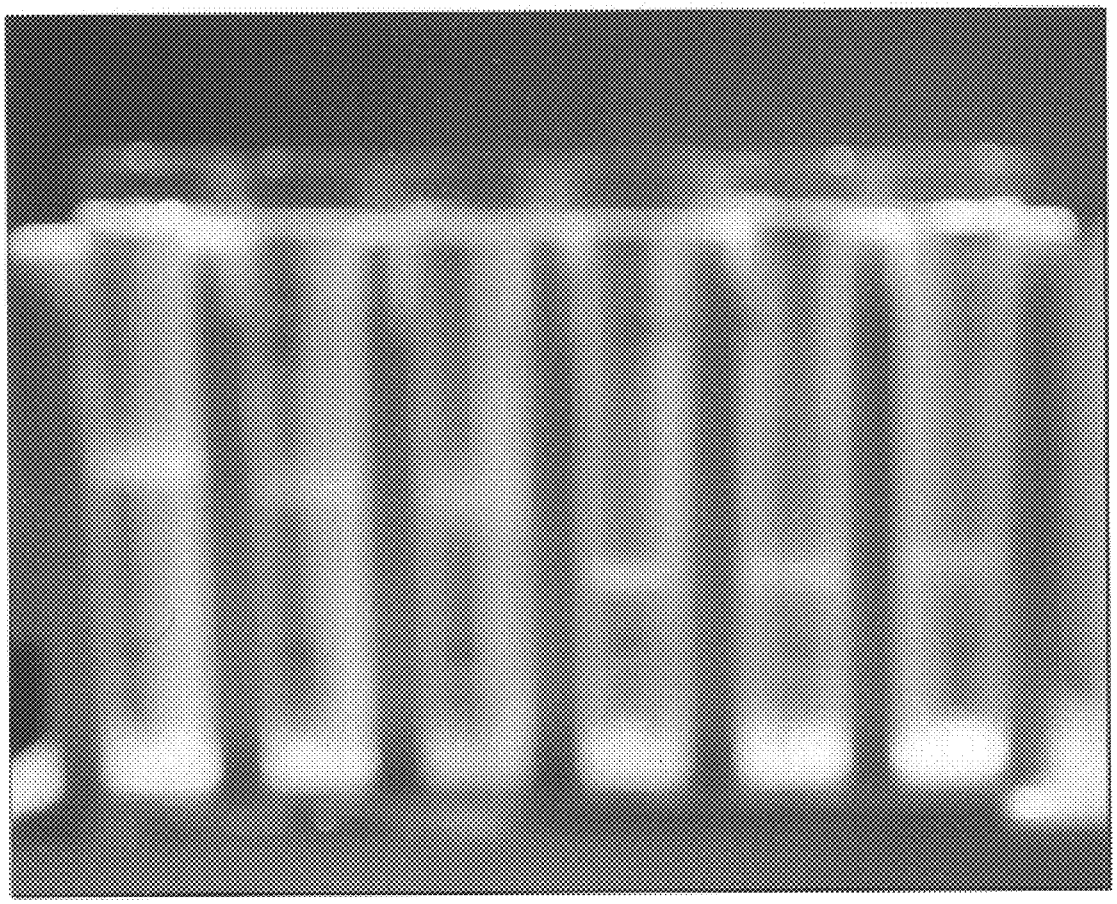
FIG. 1 is a graphical representation of bands resulting from ultracentrifugation of polynucleotide-liposome complexes on a sucrose gradient.

The invention separates defined, active complexes formed by the association of a polynucleotide associated with a transfecting component by a particular physicochemical characteristic of the complex. Suitable transfecting components include lipids, cationic lipids, peptide, cationic peptides, carbohydrates, dendrimers or polycations.

A wide variety of polynucleotide complexes may be prepared with the separation techniques of this invention. The polynucleotide may be a single-stranded DNA or RNA, or a double-stranded DNA or DNA-RNA hybrid. Triple- or quadruple-stranded polynucleotides with therapeutic value are also contemplated to be within the scope of this invention. Examples of double-stranded DNA include structural genes, genes including operator control and termination regions, and self-replicating systems such as plasmid DNA, among others.

Single-stranded polynucleotides or "therapeutic strands" include antisense polynucleotides (DNA and RNA), ribozymes and triplex-forming oligonucleotides. In order to have prolonged activity, the therapeutic strand preferably has as some or all of its nucleotide linkages stabilized as non-phosphodiester linkages. Such linkages include, for example, phosphorothioate, phosphorodithioate, phosphoroselenate, or O-alkyl phosphotriester linkages wherein the alkyl group is methyl or ethyl, among others.

For these single-stranded polynucleotides, it may be preferable to prepare the complementary or "linker strand" to the therapeutic strand as part of the administered composition. The linker strand is usually synthesized with a phosphodiester linkage so that it is degraded after entering the cell. The "linker strand" may be a separate strand, or it may be covalently attached to or a mere extension of the therapeutic strand so that the therapeutic strand essentially doubles back and hybridizes to itself. Alternatively, the linker strand may have a number of arms that are complementary so that it hybridizes to a plurality of polynucleotide strands.

The linker strand may also have functionalities on the 3' or 5' end or on the carbohydrate or backbone of the linker that serve as functional components to enhance the activity of the therapeutic strand. For example, the phosphodiester linker strand may contain a targeting ligand such as a folate derivative that permits recognition and internalization into the target cells. If the linker is attached to its complementary therapeutic strand that is composed of degradation-resistant linkages, the duplex would be internalized. Once inside the cell, the linker will be degraded, thereby releasing the therapeutic strand. In this manner, the therapeutic strand will have no additional functionalities attached and its function will not be impeded by non-essential moieties. This strategy can be applied to any antisense, ribozyme or triplex-forming polynucleotide and it is used to deliver anti-viral, antibacterial, anti-neoplastic, anti-inflammatory, anti-proliferative, anti-receptor blocking or anti-transport polynucleotides, and the like.

A separate linker strand may be synthesized to have the direct complementary sequence to the therapeutic strand and hybridize to it in a one-on-one fashion. Alternatively, the linker strand may be constructed so that the 5' region of the linker strand hybridizes to the 5' region of the therapeutic strand, and the 3' region of the linker strand hybridizes to the 3' region of the therapeutic strand to form a concatenate of the following structure.

5' _ _ _
3' _ _ _

This concatenate has the advantage that the apparent molecular weight of the therapeutic nucleic acids is increased and its pharmacokinetic properties and targeting ligand:therapeutic oligonucleotide ratio can be adjusted to achieve the optimal therapeutic effect. The linker strand may also be branched and able to hybridize to more than one copy of the polynucleotide. Other strategies may be employed to deliver different polynucleotides concomitantly. This would allow multiple genes to be delivered as part of a single treatment regimen.

The transfecting component associated with the polynucleotide may comprise a peptide, a cationic peptide, a lipid including cationic lipids, a liposome or lipidic particle, a carbohydrate, a polycation such as polylysine, a branched polycation such as a dendrimer and the compositions found in U.S. patent applications Ser. No. 08/092,200, filed Jul. 14, 1992, and Ser. No. 07/913,669, filed Jul. 14, 1993, (incorporated above) or other components that facilitate gene transfer.

In a preferred embodiment, cationic liposomes are mixed with a polynucleotide at various conditions to form polynucleotide-liposome complexes. A linear sucrose gradient of 0–30% concentration is prepared using by freezing and thawing a 15% sucrose solution 4 to 6 times. The polynucleotide-liposome complexes are loaded at the top of the gradient and ultra centrifuged for 18 hours at 40,000 rpm at a specific temperature. The gradient processing causes the different complexes, along with free liposomes and free DNA molecules migrate to specific positions in the gradient according to their density. Different bands are detected by visual observation, as well as other optical or chemical measurements. Free liposomes usually stay at the top (0–3%) due to their low density, while free polynucleotides travel to the bottom (>25%). Active complexes of the polynucleotide and liposomes, with an intermediate density between the individual components, form discrete bands in the middle of the gradient (10%–20%) as shown in FIG. 1. The active complexes of this invention migrate to two major bands, corresponding to two different liposome-polynucleotide compositions: a lighter complex at 10–13% sucrose concentration, and a heavier complex at 16–19% sucrose concentration. Besides these two major bands, other bands may occasionally appear, especially when the liposomes and polynucleotide are mixed at charge ratios close to 1/1. Such bands are either very faint or unstable and do not correspond to predicable, specific liposome-polynucleotide interaction.

Other centrifuge gradients are suitable for the practice of this invention. Non-ionic glucose, lactose and glycerol and others are useful. In particular, a Ficoll™ gradient may be used. In addition, discontinuous or step gradient may be used to enable rapid separation. For instance, a ficoll step gradient comprising a lower solution of 17% and an upper solution of 7% can be used to successful separate active complexes from excess components. Excess liposomes stay on top of the 7% phase, active complexes concentrate at the interface, and free DNA migrates to the bottom of the 17% phase. Other step or discontinuous gradients may be used, with the concentrations selected to efficiently separate the active complexes. The exact percentages will depend of the physical characteristics of the active compound and the components of the gradient. The centrifuge regimen also may be tailored as desired, varying the speed, time and temperature. In particular, for large scale separations, it may be desirable to employ continuous flow centrifugation regimens. This may be particularly useful in commercial applications. Polynucleotide-transfecting component complexes may also be identified by separation using cross flow electrophoresis. Other two-dimensional electrical separation regimes may be employed.

Characterization of the active complexes separated by the invention indicates the complexes within a particular band correspond to a specific polynucleotide-transfection component interaction. The active complexes were separated by ultra centrifuging a cationic liposome-DNA mixture across a sucrose gradient as described above. Following resolution, the gradient was fractionated and each fraction assayed for its lipid-DNA composition and characterized for the complex physico-chemical properties. Fluorescence labeled lipid (Rh-PE) was used to assay lipid distribution and DNA extraction used to determine DNA concentration for each fraction. The profiles of the PE-DNA complexes formed at a range of cationic lipid:polynucleotide charge ratios were determined, from 16:1 to 1:8, and the results are displayed in FIG. 2. Positively charged active complexes were formed when DNA was mixed with an excess of cationic liposomes, that is, at charge ratios greater than 1:1. The major band corresponding to these complexes locates at about an 11% sucrose concentration. Increasing amounts of free liposomes were found at the top of the gradient for the higher charge ratio mixtures. Negatively charged active complexes were formed when an excess of DNA was mixed with cationic liposome, that is, at charge ratios less than 1:1. The major band corresponding to these complexes locates at about a 17% sucrose concentration. Similarly, increasing amounts of free DNA were found at the bottom of the gradient at lower charge ratios. At charge ratios closer to 1:1, the chance of minor bands resolving increases. However, these bands were barely visible and do not appear to correspond to complexes formed by specific interactions. The major bands appeared consistently at the two specific positions, depending on charge of the formed active complexes and was not affected by the exact initial charge ratios. Mixtures of lipid and polynucleotide at a charge ratio of 1:1 resulted in precipitation following centrifugation, and the position of any bands varied, presumably due to the experimental variation in mixing exact 1:1 complexes.

Figure 3:
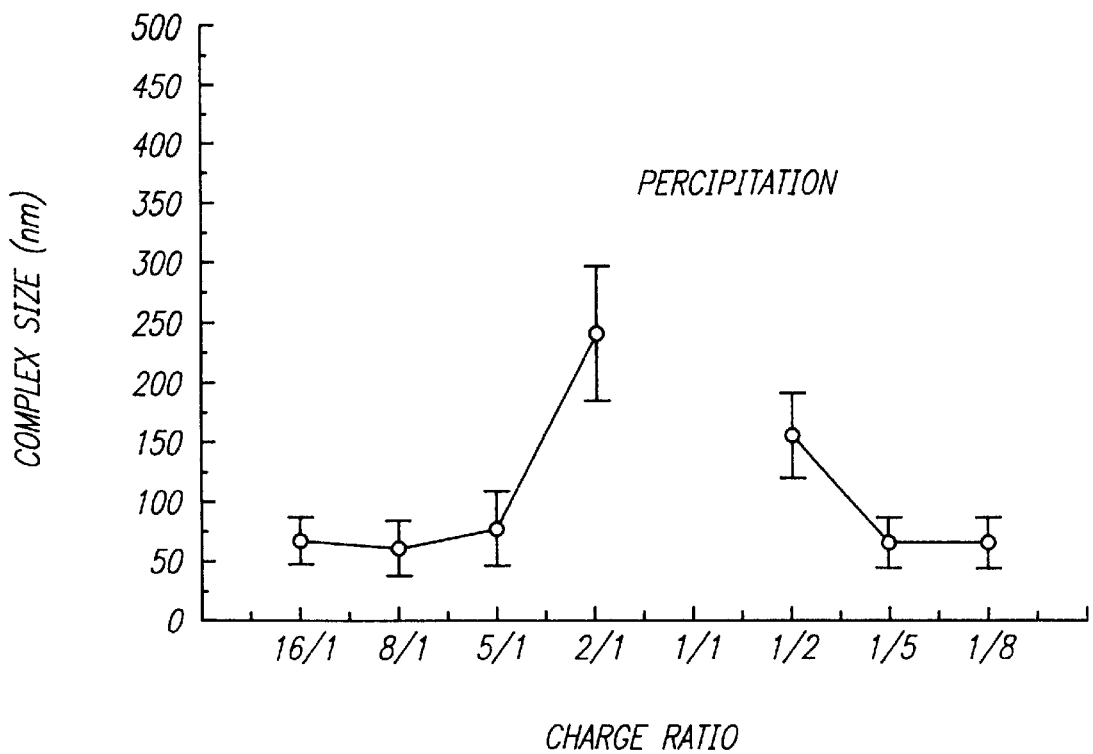
FIG. 3 relates the particle size distribution of gradient processed polynucleotide-liposome complexes to charge ratio.

FIG. 3 plots the zeta-potential of the active complexes formed at varying charge ratios. Positively charged complexes formed at excesses of cationic liposomes exhibit zeta-potentials ranging between about 20–30 mV, increasing only slightly with greater charge ratios. Negatively charged complexes formed at excesses of DNA exhibit a zeta-potential of about −30 mV, virtually independent of exact initial charge ratio. The observed polarized profiles indicate that a specific interaction between the liposome and polynucleotide components produces each active complex.

Figure 4:
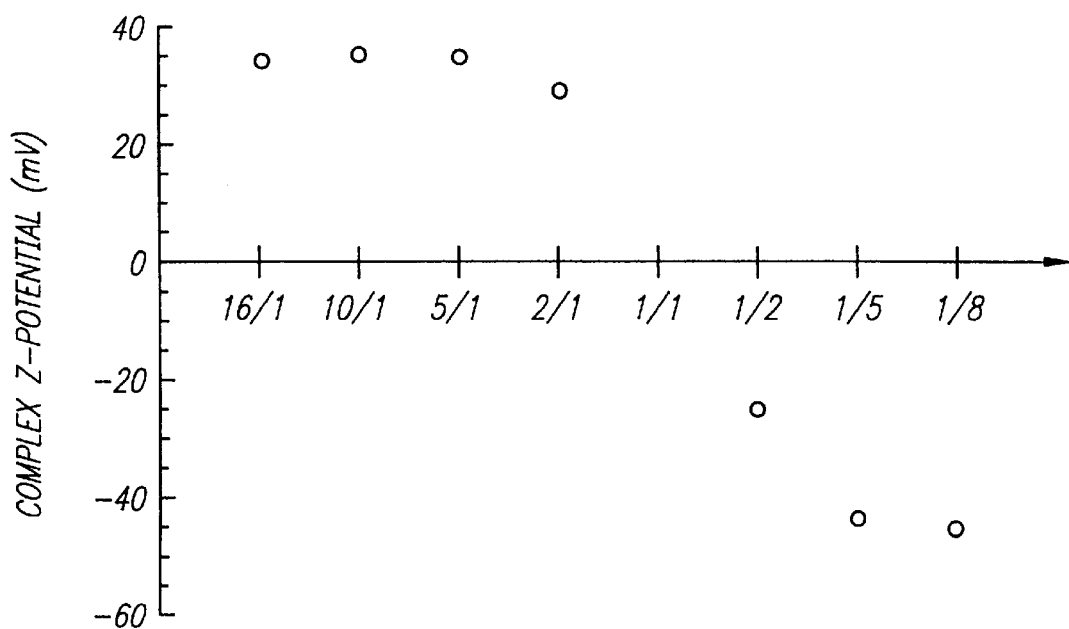
FIG. 4 illustrates the zeta potential of gradient processed polynucleotide-liposome complexes at various charge ratios.

FIG. 4 plots the size distribution of active complexes formed at varying charge ratios. At charge ratios greater than about 5:1 and less than about 1:5, the active complexes have an average particle size of approximately 60 nm. These results were observed even at high mixing concentrations, such as up to 1 mg/ml DNA. Complexes formed at ratios of 2:1 and 1:2 had greater average particle sizes, and at ratios close to 1:1 the mixture precipitates. The complex size varies among different mixing charge ratios, as expected for polyelectrolyte interaction. As the charge ratios approach 1:1, the polynucleotide of each complex may have unprotected areas capable of cross-linking with each other, forming weak aggregations which increase the average particle size. Nevertheless, these results also indicate that the active complexes correspond to specific interactions between the polynucleotide and transfecting component.

The stability of the complexes formed at large excess of either liposome or DNA after gradient separation is very good; their mean diameters remain unchanged for more than one month. The gradient separation procedure seems to accelerate the precipitation process if the complex is not stable, especially when the charge ratio of the mixture is around 1:1, probably due to the forces developed during centrifugation.

The active complexes obtained by the separation procedure are useful for transferring the complexed polynucleotide to target cells. Conventional practices have large amounts of excess component and present daunting cytotoxicity problems at high complex concentrations. The separation procedure avoids these problems by isolating the active complex. For example, the positively charged active complexes of this invention may be formulated at polynucleotide concentrations as high as 1000 μg/ml. Conventional formulations at this concentration are infeasible due to instability and cytotoxicity. Concentrations for negatively charged active complexes range as high as 1000 μg/ml. The transfection efficiency of the active complexes of this invention was compared to that of non-gradient processed polynucleotide-liposome mixture. Both positively charged complexes separated from high charge ratio mixtures and negatively charged complexes separated from mixtures with excess DNA were used to test transfection activity in vitro.

A conventional transfection procedure was followed. Cells were plated 24 hours before transfection. Active polynucleotide-lipid complexes of plasmid DNA encoding β-galactosidase reporter gene driven by CMV promoter (CMV-β-gal) and cationic liposomes were separated on a sucrose gradient as described above. The complexes were added to the cell culture medium containing varied concentrations of serum and incubated for 5 hours. The medium was replaced with a medium containing 10% serum. After 48 hours, the cells were harvested and assayed for reporter gene activity.

As shown in FIG. 4, positively charged active complexes have much higher activity than the conventional liposome-DNA complexes that did not undergo ultra centrifugation separation at normal doses and equivalent to the activity of the unprocessed complexes at optimal transfection conditions. Doubling the dose of the unprocessed complexes does not improve the activity because of the toxicity effect. Conversely, gradient processing allowed the concentration of the active complexes to be doubled, substantially increasing the activity. All positively charged complexes exhibited diminished activity when serum was present in the transfection medium, but activity was recovered and even improved at 10% serum concentration by using gradient processed active complexes and by increasing the dose. Further increase of serum content decreases activity, with only a small amount remaining at 30% serum concentration, even at high DNA doses.

Negatively charged active complexes exhibit significantly improved activity over unprocessed complexes, but the absolute activity of negatively charged active complexes is low compared to positively charged active complexes. However, the negatively charged active complexes maintain significant activity at serum concentrations up to 30% and activity was correlated with dose as shown in FIG. 5. These distinctive properties may make the negatively charged active complexes desirable for certain applications.

The active complexes isolated using the separation methods of this invention offer a number of advantages: active complexes can offer greater transfective activity at equivalent doses; higher concentrations of the complexes can be used without cytotoxic effect; and the complexes have small particle size as well as greatly enhanced stability and uniformity. These characteristics make the active complexes also well suited to in vivo protocols.

Conventional cationic lipids suitable for the practice of the invention include phosphatidylethanolamine [PE], dioleyloxy phosphatidylethanolamine [DOPE], n-[1-(2,3-dioleyloxy)propyl]-N,N,N-trimethylammonium chloride [DOTMA], dioleoylphosphatidylcholine [DOPC], 2,3-dioleyloxy-N-[2-(sperminecarboxyamido)ethyl]-N,N-dimethyl-1-propanaminium trifluoroacetate [DOSPA], [DOTAP], [DOGG], dimethyldioctadecylammonium bromide [DDAB], cetyldimethylethylammonium bromide [CDAB], cetyltrimethylethylammonium bromide [CTAB], monooleoyl-glycerol [MOG], 1,2 dimyristyloxypropyl-3-dimehtyl-hydroxyethyl ammonium bromide [DMRIE], 1,2 dimyristoyl-sn-glycero-3-ethylphosphocholine [EDMPC], 1,2 dioleoyl-sn-glycero-3-ethylphosphocholine [EDOPC], 1 palmitoyl, 2 myristoyl-sn-glycero-3-ethylphosphocholine [EPMPC], cholesterol [Chol] and cationic bile salts. Other useful cationic lipids may be prepared in the following manners.

Figure 7:
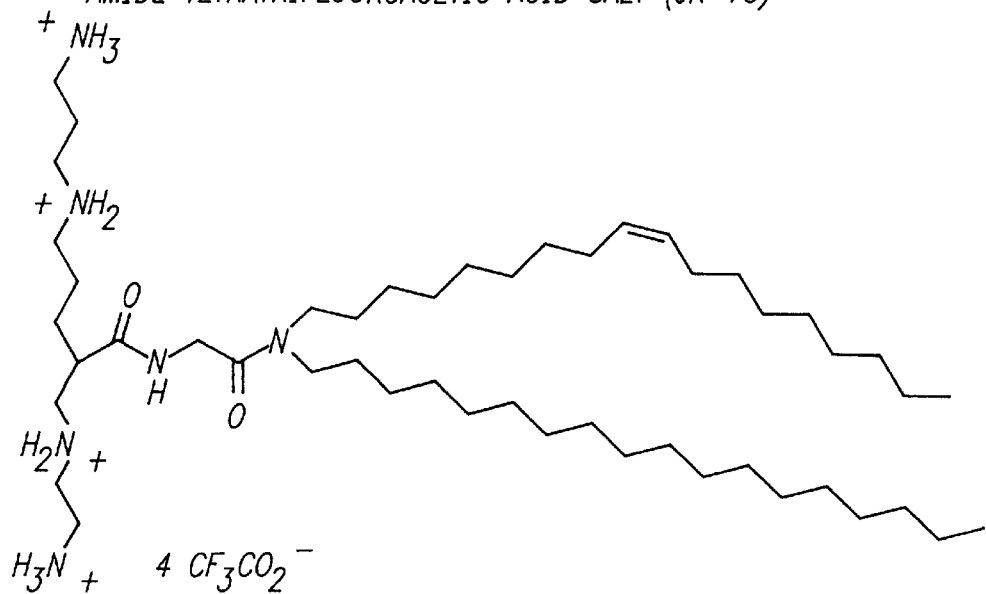

Spermine-5-carboxyglycine (N'-stearyl-N'-oleyl) amide tetratrifluoroacetic acid salt (JK-75) FIG. 7.

A p-nitrophenyl oleinate ester was prepared by a standard method. This active ester coupled with octadecylamine to give N-octadecyl oleic amide. Reduction of this amid by lithium aluminum hydride formed N-stearyl N-oleyl amine. A mixture of N-stearyl N-oleyl amine, N-butoxycarbonylglycine p-nitrophenyl ester, and triethylamine in dichloromethane was stirred at room temperature under argon for 24 h. The organic solution was extracted three times with 0.5 M sodium carbonate, followed by water, and then dried over sodium sulfate. The solvent was removed under reduced pressure, and the residue was purified by a silica gel flash column to give N-t-butoxycarbonylglycine (N'-stearyl-N'-oleyl) amide. This compound was deprotected by trifluoroacetic acid to give glycine (N'-stearyl-N'-oleyl) amide, which was then treated with tetra-t-butoxycarbonylspermine-5-carboxylic acid (prepared by the cyanoethylation of ornitine, followed by a hydrogenation and protection with Boc-on), dicyclohexylcarbodiimide and N-hudroxysuccinimide in dichloromethane in dark at room temperature under argon for 48 h. The solvent was removed under reduced pressure, and the residue was purified by a silica gel column. The desired compound was then deprotected in trifluoroacetic acid at room temperature for 10 min. The excess of acid was removed under vacuum to yield the spermine-5-carboxyglycine (N'-stearyl-N'-oleyl) amide tetra trifluoroacetic acid salt, as a light yellow wax. $^1$H NMR (300 Mhz, CD$_3$OD) δ 5.20 (m, 2 H), 4.01 (s, 2 H), 3.87 (t, 1 H), 3.19–2.90 (m, 16 H), 2.01–1.27 (m, 21 H), 1.15 (broad s, 56 H), 0.76 (t, 6 H). LSIMS (NBA): m/e 805.8 for M$^{4+}$ (C$_{49}$H$_{104}$N$_6$O$_2$)-3H$^+$.

Figure 8:
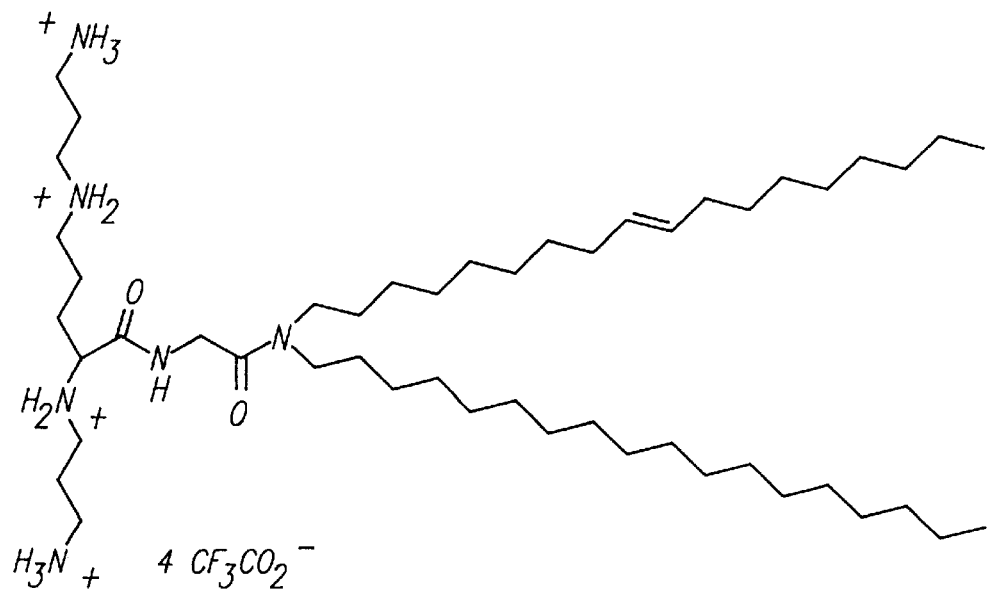

Spermine-5-carboxyglycine (N'-stearyl-N'-elaidyl) amide tetratrifluoroacetic acid salt (JK-76). FIG. 8.

Figure 9:
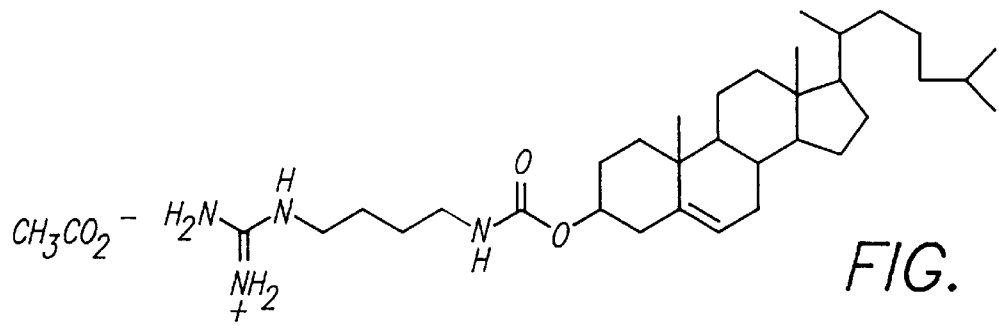

Produced in a similar manner, by substituting for the appropriate starting material. $^1$H NMR (300 MHz, CD$_3$OD): δ 5.24 (m, 2 H), 4.01 (s, 2 H), 3.87 (t, 1 H), 3.14–2.90 (m, 16 H), 2.01–1.21 (m, 21 H), 1.15 (broad s, 56 H), 0.76 (t, 6 H). LSIMS (NBA): m/e 805.8 for M$^{4+}$ (C$_{49}$H$_{104}$N$_6$O$_2$)-3H$^+$ Agmatinyl carboxycholesterol acetic acid salt (AG-Chol) FIG. 9.

Agmatine sulfate (100 mg, 0.438 mmol) was treated by tetramethylamonium hydroxide (158 mg, 0.876 mmol) in methanol (15 ml) for 1 h. The solvent was removed under reduced pressure. A suspension solution of the residue and cholesteryl chloroformate (197 mg, 0.438 mmol) in DMF (15 ml) was stirred at room temperature for 3 days. Filtration of the reaction mixture gave the crude product as a light yellow solid, which was purified by a silica gel column using chloroform-methanol-acetic acid (10:2:1) as eluent to yield the agmatinyl carboxycholesterol acetic acid salt as a white solid. $^1$H NMR (300 MHz, CD$_3$OD): δ 5.27 (broad s, 1 H), 4.65 (broad m, 1 H), 3.06 (t, 2 H), 2.99 (t, 2 H), 2.21 (broad d, 2 H), 1.95–0.65 (m, 31 H), 1.80 (s, 4 H), 0.91 (s, 3 H), 0.82 (d, 3 H), 0.76 (s, 3 H), 0.74 (s, 3 H), 0.59 (s, 3 H). LSIMS (NBA): m/e 543.4 for M+ (C$_{33}$H$_{59}$N$_4$O$_2$).

Figure 10:
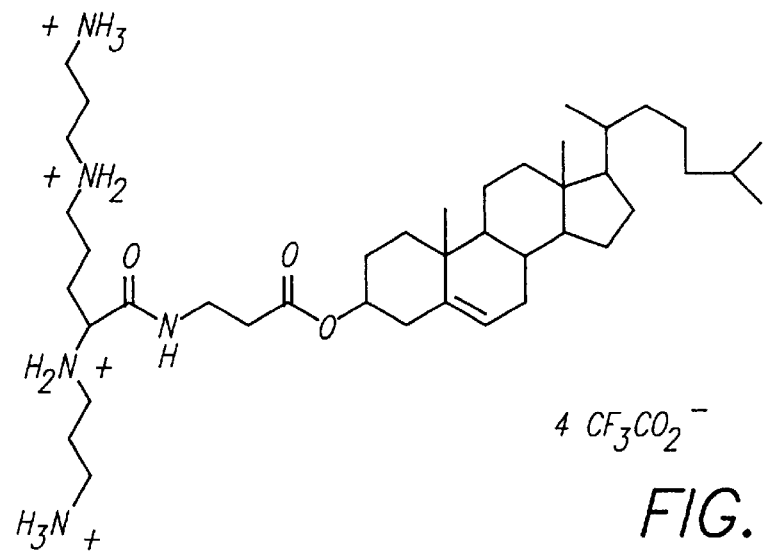

Spermine-5-carboxy-β-alanine cholesteryl ester tetratrifluoroacetic acid salt (CAS) FIG. 10.

A solution of cholesteryl β-alanine ester (0.2 mmol), prepared with standard procedure, in dichloromethane (dry, 2 ml) was added into a solution of tetra-t-butoxycarbonylspermine-5-carboxylic acid N-hydroxysuccinimide ester (0.155 mmol) and 4-methylmorpholine (0.4 ml) in dichloromethane (5 ml). The reaction mixture was stirred at room temperature under argon for 6 days. The solvent was removed under reduced pressure, and the residue was purified by a silica gel column using ethanol-dichloromethane (1:20) as eluent to give the desired product as a light yellow oil. This compound was treated with trifluoroacetic acid (0.5 ml) at room temperature under argon for 10 min. The excess trifluoroacetic acid was removed under reduced pressure to give spermine-5-carboxy-β-alanine cholesteryl ester tetratrifluoroacetic acid salt as a white solid. $^1$H NMR (300 MHz, CDCl$_3$): δ 5.38 (m, 1 H), 4.60 (m, 1 H), 3.90 (t, J=6.16, 1 H), 3.54 (m, 2 H), 3.04 (m, 10 H), 2.58 (t, J=6.71, 2 H), 2.33 (d, J=6.58, 2 H), 2.15–0.98 (m, 36 H), 1.04 (s, 3 H), 0.93 (d, J=6.46, 3 H), 0.87 (d, J=6.59, 6 H), 0.70 (s, 3 H). LSIMS (NBA): m/e 687.5 for M$^{4+}$ (C$_{41}$H$_{80}$N$_5$O$_3$)-3H$^+$.

Figure 11:
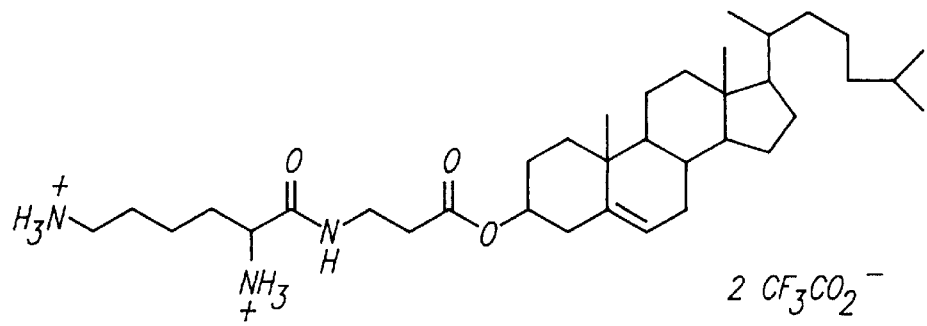

2,6-Diaminohexanoeyl β-alanine cholesteryl ester bistrifluoroacetic acid salt (CAL) FIG. 11.

Produced in a manner similar to CAS, by substituting for the appropriate starting material.

$^1$H NMR (300 MHz, CDCl$_3$): δ 8.10–7.62 (m, 7 H), 5.38 (broad s, 1 H), 4.60 (broad s, 1 H), 4.08 (broad s, 1 H), 3.40 (broad s, 4 H), 3.02 (broad s, 4 H), 2.50 (broad s, 2 H), 2.26 (broad s, 2 H), 2.04–0.98 (m, 28 H), 1.04 (s, 3 H), 0.93 (d, J=6.46, 3 H), 0.88 (d, J=6.59, 6 H), 0.74 (s, 3 H). LSIMS (NBA): m/e 586.5 for M$^{2+}$ (C$_{36}$H$_{65}$N$_3$O$_3$)-H$^+$.

2,4-Diaminobutyroyl β-alanine cholesteryl ester bistrifluoroacetic acid salt (CAB) FIG. 12.

Produced in a manner similar to CAS, by substituting for the appropriate starting material.

$^1$H NMR (300 MHz, CDCl$_3$): δ 8.34–8.06 (m, 7 H), 5.38 (broad s, 1 H), 4.60 (broad s, 1 H), 4.30–3.20 (broad m, 11 H), 2.50–0.98 (m, 36 H), 1.04 (s, 3 H), 0.93 (d, J=6.46, 3 H), 0.88 (d, J=6.59, 6 H), 0.74 (s, 3 H). LSIMS (NBA): m/e 558.5 for M$^{2+}$ (C$_{34}$H$_{61}$ N$_3$O$_3$)-H$^+$.

N,N-Bis (3-aminopropyl)-3-aminopropionyl β-alanine cholesteryl ester tristrifluoroacetic acid salt (CASD) FIG. 13.

Cyanoethylation of the β-alanine with acrylnitrile in the presence of 1,4-diazabicyclo [2.2.2] octane at 90° C. for 15 h gave the N,N-bis(2-cyanoethyl)-3-aminopropionic acid. Hydrogenation of the N,N-bis(2-cyanoethyl)-3-aminopropionic acid in ethanol-water (1:1) using Raney nickel as catalyst yielded the N,N-bis(3aminoethyl)-3-aminopropionic acid. The amino groups of this compound was protected by 2-(t-butoxycarbonyloxylmino)-2-phenylacetonitrile in acetone-water (4:1) to give N,N-bis (t-butoxycarbonyl-3-animoethyl)-3-aminopropionic acid. This compound was activated by chloroacetonitrile and triethylamine to form cyanomethyl N,N-bis (t-butoxycarbonyl-3-animoethyl)-3-aminopropionate. A solution of the cyanomethyl ester and cholesteryl β-alanine ester in chloromethane was stirred in dark at room temperature under argon for 10 days. The solvent was removed under reduced pressure, and the residue was purified by a silica gel column using methanol-chloroform (1:10) as eluant to yield the N,N-bis (t-butoxycarbonyl-3-aminoethyl)-3-aminopropionoyl β-alanine cholesteryl ester. Treatment of this compound with trifluoroacetic acid formed N,N-bis (3-aminopropyl)-3-aminopropionoyl β-alanine cholesteryl ester tristrifluoroacetic acid salt. $^1$H NMR (300 MHz, CD$_3$OD-CDCl$_3$ 1:1): δ 8.13 (broad s, 3 H), 5.78 (broad s, 3 H), 5.38 (broad s, 1 H), 5.18 (s, 1H), 4.74 (s, 1 H), 4.60 (broad s, 1 H), 3.54–3.04 (m, 10 H), 2.80 (t, J=6.60, 2 H), 2.73 (t, J=6.54, 2 H), 2.53(t, J=6.42, 2 H), 2.32(d, J=6.58, 2 H), 2.15–0.98 (m, 30 H), 1.04 (s, 3 H), 0.91 (d, J=6.42, 3 H), 0.86 (d, J=6.58, 6 H), 0.70 (s, 3 H). LSIMS (NBA): m/e 643.5 for M$^{3+}$ (C$_{39}$H$_{73}$N$_4$O$_3$)-2H

[N,N-Bis(2-hydroxyethyl)-2-aminoethyl]aminocarboxy cholesteryl ester (JK-154) FIG. 14.

A solution of cholesteryl chloroformate (0.676 g, 1.51 mmol) and ethelenediamine (4 ml) in chloroform (10 ml) was stirred in dark at room temperature under argon for 16 h. The solvent and excess of ethylendiamine were removed under reduced pressure, and the residue was purified by a silica gel column using CH$_3$OH—CHCl$_3$ (NH$_3$) (v/v, 0–20%) as eluent to give ethylendiamine cholesterylcarboxymonoamide as a white solid. A mixture of this compound (80 mg, 0.17 mmol), 2-hydroxyethylbromide (2 mg) and triethylamine (2 ml) was stirred in dark at room temperature under argon for 14 days. The excess of triethylamine and 2-hydroxyethylbromide were removed under reduced pressure, and the residue was purified by a silica gel column using CH$_3$OH—CHCl$_3$ (v/v, 1:3) as eluent to give the 2-[N,N-Bis(2-hydroxyethyl) aminoethyl] amino carboxy cholesteryl ester as a white solid. $^1$H NMR (300 MHz, CDCl$_3$): δ LSIMS (NBA): m/e 643.5 for M$^{3+}$ (C$_{39}$H$_{73}$N$_4$O$_3$)-2H$^+$.

Carnitine ester lipids

Carnitine lipids are synthesized by acylating the hydroxy group of L-carnitine by standard methods to create the monoacyl carnitine. The carboxy group of the carnitine is modified with a second acyl chain to make a phospholipid analog with a single quarternary ammonium cationic group. The other carnitine stereoisomers D- and D,L- are suitable, but the L-form is preferred. The acyl chains are between 2 and 30 carbons and may be saturated or unsaturated, with from 1 to 6 unsaturated groups in either the cis or trans configuration. The acyl chains may also contain iso forms. A preferred form comprises the oleoyl group, a chain 18 carbons long with a cis unsaturated bond at C$_9$. This generic carnitine ester is shown in FIG. 15. Presently preferred carnitine esters follow.

Stearyl carnitine ester

A solution of DL-carnitine hydrochloride (1.0 g, 5.05 mmol) and sodium hydroxide (0.303 g, 7.58 mmol) in ethanol (15 ml) was stirred at room temperature for 2 h. The formed white precipitate (NaCl) was removed by filtration, and the solvent was evaporated under reduced pressure to give a white solid, carnitine inner salt. A suspension of the carnitine inner salt and 1-iodooctadecane (2.31 g, 6.06 mmol) in DMF-dioxane (3:5, 40 ml) was heated with an oil-bath at 120° C. under Ar$_2$ for 4 h. The solvent was removed by rotavapor and vacuum, and the residue was chromatographied with silica gel column using CH$_3$OH—CH$_3$Cl as eluant to give 2.22 g (81%) of stearyl carnitine ester as a white solid: $^1$H NMR (CDCl$_3$) δ 4.79 (m, 1 H), 4.43 (d, J=5.3, 1 H), 4.09(t, J=6.9, 2 H), 4.03 (d, J=13.o, 1 H), 3.67 (dd, J=10.3, 13.3, 1 H), 3.51 (s, 9 H), 2.79 (dd, J=5.7, 17.0, 1 H), 2.66 (dd, J=7.0, 17.1, 1 H), 1.80–1.60 (m, 4 H), 1.26 (broad s, 28 H), 0.88 (t, J=6.6, 3 H). LSIMS (NBA): m/e 414.4 for C$_{25}$H$_{52}$NO$_3$ (cation).

Palmityl carnitine ester

With the procedure used for the preparation of stearyl carnitine ester, 0.77 g (4.77 mmol) of carnitine inner salt and 2.52 g (7.15 mmol) of 1-iodohexadecane to give 1.59 g (65%) of palmityl carnitine ester as a white solid: $^1$H NMR (CDCl$_3$) δ 4.78 (m, 1 H), 4.44 (d, J=5.4, 1 H), 4.09 (t, J=6.9, 2 H), 3.65 (dd, J=10.2, 13.3, 1 H), 3.58 (d, J=5.1, 1 H), 3.51 (broad s, 9 H), 2.80 (dd, J=5.7, 17.2, 1 H), 2.66 (dd, J=7.1, 17.1, 1 H), 1.65 (broad m, 4 H), 1.26 (broad s, 24 H), 0.88 (t, J=0.66, 3 H). LSIMS (NBA): m/e 386.2 for C$_{23}$H$_{48}$NO$_3$ (cation).

Myristyl carnitine ester

With the procedure used for the preparation of stearyl carnitine ester, 0.77 g (4.77 mmol) of carnitine inner salt and 2.31 g (7.15 mmol) of 1-iodotetradecane gave 1.70 (74%) of myristyl carnitine ester as a white solid: $^1$H NMR (CDCl$_3$) δ 4.79 (m, 1 H), 4.43 (d, J=5.3, 1 H), 4.09(t, J=6.9, 2 H), 4.03

(d, J=13.o, 1 H), 3.67 (dd, J=10.3, 13.3, 1 H), 3.51 (s, 9 H), 2.79 (dd, J=5.7, 17.0, 1 H), 2.66 (dd, J=7.0, 17.1, 1 H), 1.80–1.60 (m, 4 H), 1.26 (broad s, 20 H), 0.88 (t, J=6.6, 3H). LSIMS (NBA): m/e 358.1 for $C_{21}H_{44}NO_3$ (cation).

Stearyl stearoyl carnitine ester chloride salt (SSCE) FIG. 16.

A solution of DL-carnitine hydrochloride (1.0 g, 5.05 mmol) and sodium hydroxide (0.303 g, 7.58 mmol) in ethanol (15 mg) was stirred at room temperature for 2 h. The formed white precipitate (NaCl) was removed by filtration, and the solvent was evaporated under reduced pressure to give a white solid, carnitine inner salt. A suspension of the carnitine inner salt and 1-iodooctadecane (2.31 g, 6.06 mmol) in DMF-dioxane (3:5, 40 ml) was heated with an oil-bath at 120° C. under argon for 4 h. The solvent was removed under reduced pressure, and the residue was purified by a silica gel column using $CH_3OH$—$CH_3Cl$ (v/v, 0–10%) as eluent to give the stearyl carnitine ester as a white solid. A solution of a fresh prepared stearic anhydride (1.94 g, 3.52 mmol), stearyl carnitine ester (0.953 g, 1.76 mmol) and 4-dimethylaminopyridine (0.429 g, 3.52 mmol) in $CH_3Cl$ (dry, 15 ml) was stirred at room temperature under argon for four days. The solvent was removed under reduced pressure, and the residue was washed twice by cold diethyl ether. The solid was chromatographied on a silica gel column using MeOH—$CHCl_3$ (v/v, 1:5) as eluent to give the stearyl stearoyl carnitine ester iodide. The iodide was exchanged by chloride with an anion exchange column to give the stearyl stearoyl carnitine ester chloride as a white solid. $^1$H NMR (300 MHz, $CDCl_3$) δ 5.67 (q, 1 H), 4.32 (d, 1 H), 4.07 (m, 3 H), 3.51 (s, 9 H), 2.82 (t, 2 H), 2.33 (t, 2 H), 1.59 (broad m, 4 H), 1.25 (broad s, 58 H), 0.88 (t, 6 H). LSIMS (NBA): m/e 680.6 for $M^+$ ($C_{43}H_{86}NO_4$). Anal. Calcd for $C_{43}H_{86}ClNO_4 \cdot H_2O$: C, 70.30; H, 12.07; N, 1.91. Found: C, 70.08; H, 12.24; N, 1.75.

L-Stearyl Stearoyl Carnitine Ester (L-SSCE) was prepared with the same procedure using L-carnitine as starting material. Analytical data are same as DL-SSCE.

Stearyl oleoyl carnitine ester chloride (SOCE) FIG. 17.

Prepared in a manner similar to SSCE, by substituting the appropriate starting material.

$^1$H NMR (300 MHz, $CDCl_3$): δ 5.67 (q, 1 H), 5.35 (m, 2 H), 4.32 (d, 1 H), 4.08 (m, 3 H), 3.48 (s, 9 H), 2.83 (dd, 2 H), 2.34 (dd, 2 H), 2.02 (broad m, 4 H), 1.26 (broad m, 54 H), 0.88 (t, 6 H). LSIMS (NBA): m/e 678.7 for M+ ($C_{43}H_{84}NO_4$). Anal. Calcd for $C_{43}H_{84}ClNO_4 \cdot H_2O$: C, 70.50; H, 11.83; N, 1.91. Found: C, 70.77; H, 12.83; N, 1.93.

Palmityl palmitoyl carnitine ester chloride (PPCE) FIG. 18.

Prepared in a manner similar to SSCE, by substituting the appropriate starting material.

$^1$H NMR (300 MHz, $CDCl_3$): δ 5.67 (q, 1 H), 4.33 (d, 1 H), 4.07 (m, 3 H), 3.51 (s, 9 H), 2.82 (t, 2 H), 2.33 (t, 2 H), 1.59 (broad m, 4 H), 1.25 (broad s, 58 H), 0.99 (t, 6 H). LSIMS (NBA): m/e 680.6 for $M^+$ ($C_{43}H_{78}NO_4$). Anal. Calcd for $C_{39}H_{78}ClNO_4 \cdot H_2O$: C, 69.04; H, 11.88; N, 2.06. Found: C, 69.31; H, 11.97; N, 2.37.

Myristyl myristoyl carnitine ester chloride (MMCE) FIG. 19.

Prepared in a manner similar to SSCE, by substituting the appropriate starting material.

$^1$H NMR (300 MHz, $CDCl_3$): δ 5.67 (q, 1 H), 4.32 (d, 1 H), 4.07 (m, 3 H), 3.50 (s, 9 H), 2.82 (t, 2 H), 2.33 (t, 2 H), 1.61 (broad m, 4 H), 1.26 (broad s, 42 H), 0.88 (t, 6 H). LSIMS (NBA): m/e 568.6.7 for M+ ($C_{35}H_{70}NO_4$). Anal. Calcd for $C_{35}H_{70}ClNO_4 \cdot \frac{1}{2}H_2O$: C, 68.53; H, 11.67; N, 2.28. Found: C, 68.08; H, 11.80; N, 2.21.

L-Myristyl myristoyl carnitine ester chloride (L-MMCE) was prepared with the same procedure using L-carnitine as starting material. Analytical data are same as DL-MMCE. m.p. 157° C. (decomposed).

Complexes formed with these lipids, as well as the other complexes of the invention, can also be separated by methods that can fractionate colloids and particulates based upon size and charge differences. One such technique that is particularly useful is electrical field-flow fractionation. This technique is carried out in a thin channel (circa 200 microns) between smooth and rigid electrodes such as those prepared from graphite. The sample is applied to one end of the channel in a flowing fluid of low ionic strength. The voltage (circa 2 volts) is applied perpendicular to the flow. As the material flows through the channel the negatively charged particles are attracted to one electrode while the positively charged particles are attracted to the opposite electrode. The force attracting the particle to the respective electrode depends upon the diameter of the particle and its zeta potential. Particles that are moved towards the surface of the electrode are retained in the channel to a greater extent than particles that remain in the center of the channel. To separate active complex from the starting components one first mixes the components in the appropriate ratio. The mixture is then introduced into the channel. The flowing fluid carriers the particles through the channel; for particles of the same diameter, the particles with the greater zeta potential are retained to a greater extent than particles with a zeta potential closer to zero. For particles of the same zeta potential, the particles with the greater diameter are retained to a greater extent than are particles with a smaller diameter. In the case of the cationic lipid complexes formed with an excess of cationic liposomes, the complex elutes from the channel more rapidly than the starting cationic liposomes. In the case of the plasmid DNA-lipid complexes formed in the presence of excess DNA, the complex elutes more rapidly than the plasmid DNA. The advantage of separating the complexes using electric field flow fractionation is that the separation are rapid and the conditions can be adjusted using both the flow rate and the field strength. This technique lends it self to scale up.

Although the invention has been described primarily with reference to the presently preferred embodiment, it should be recognized that various modifications and improvements may be made that are still within the scope of the invention.

What is claimed is:

1. A method for isolating a synthetic active complex from a mixture of a polynucleotide associated with a transfecting component comprising the steps of:

a) separating the mixture into fractions of polynucleotide, transfecting component and synthetic active complex by a physical property;

b) identifying a synthetic active complex corresponding to a specific physical property; and c) isolating the synthetic active complex from free polynucleotide and excess transfecting component by extracting the synthetic active complex from the fraction corresponding to the specific physical property.

2. The method of claim 1, wherein the step of separating the mixture comprises separating the mixture by a physical property selected from the group consisting of density, particle size and surface charge.

3. The method of claim 2, wherein the step of separating the mixture comprises ultra centrifuging the mixture across a density gradient.

4. The method of claim 3, wherein the step of separating the mixture comprises ultra centrifuging the mixture across a 30% linear sucrose gradient.

5. The method of claim 4, wherein the step of extracting the synthetic active complex from a specific density fraction comprises the step of extracting the complex from a sucrose concentration between about 11% and 13%.

6. The method of claim 4, wherein the step of extracting the synthetic active complex from a specific density fraction comprises the step of extracting the complex from a sucrose concentration between about 16% and 19%.

7. The method of claim 1, wherein the step of separating the mixture comprises ultra centrifuging the mixture across a ficoll gradient.

8. The method of claim 2, wherein the step of separating the mixture comprises performing cross flow gel electrophoresis electric field flow fractionation.

9. The method of claim 1, wherein the step of mixing a polynucleotide with a transfecting component comprises mixing a polynucleotide with a cationic liposome at a charge ratio not less than 2:1.

10. The method of claim 1, wherein the step of mixing a polynucleotide with a transfecting component comprises mixing a polynucleotide with a cationic liposome at a charge ratio not greater than 1:2.

11. A product produced by the method of isolating a synthetic active complex from a mixture of a polynucleotide associated with a transfecting component comprising the steps of:
   a) mixing a polynucleotide with a transfecting component;
   b) ultra centrifuging the mixture across a density gradient to separate the mixture into fractions of polynucleotide, transfecting component and synthetic active complex;
   c) identifying a synthetic active complex corresponding to a specific density; and
   d) isolating the synthetic active complex from free polynucleotide and excess transfecting component by extracting the synthetic active complex from the density gradient.

12. The product of claim 11, wherein the transfecting component comprises a cationic liposome.

13. The product of claim 12, wherein the liposome is mixed with the polynucleotide at a charge ratio of not less than about 2:1.

14. The product of claim 13, wherein the liposome is mixed with the polynucleotide at a charge ratio of not less than about 5:1.

15. The product of claim 12, wherein the liposome is mixed with the polynucleotide at a charge ratio of not greater than about 1:2.

16. The product of claim 15, wherein the liposome is mixed with the polynucleotide at a charge ratio of not greater than about 1:5.

17. The product of claim 12, wherein the liposome is selected from the group consisting of phosphatidylethanolamine [PE], phosphatidyl choline [PC], dioleyloxy phosphatidylethanolamine [DOPE], n-[1-(2,3-dioleyloxy)propyl]-N,N,N-trimethylammonium chloride [DOTMA], dioleoylphosphatidylcholine [DOPC], 2,3-dioleyloxy-N-[2-(sperminecarboxyamido)ethyl]-N,N-dimethyl-1-propanaminium trifluoroacetate [DOSPA], [DOTAP], [DOGG], spermine-5-carboxyglycine(N'-stearyl-N'-stearyl) amide tetra-trifluoroacetic acid salt [DOGS], 1,2 dimyristyloxypropyl-3-dimehtyl-hydroxyethyl ammonium bromide [DMRIE], 1,2 dimyristoyl-sn-glycero-3-ethylphosphocholine [EDMPC], 1,2 dioleoyl-sn-glycero-3-ethylphosphocholine [EDOPC], 1 palmitoyl, 2 myristoyl-sn-glycero-3-ethylphosphocholine [EPMPC], dimethyldioctadecylammonium bromide [DDAB], cetyldimethylethylammonium bromide [CDAB], cetyltrimethylethylammonium bromide [CTAB], ], monooleoylglycerol [MOG], cholesterol [Chol], cationic bile salts, spermine-5-carboxyglycine (N'-stearyl-N'-oleyl) amide tetratrifluoroacetic acid salt [JK-75], spermine-5-carboxyglycine (N'-stearyl- N'-elaidyl) amide tetratrifluoroacetic acid salt [JK-76], agmatinyl carboxycholesterol acetic acid salt [AG-Chol], spermine-5-carboxy-β-alanine cholesteryl ester tetratrifluoroacetic acid salt [CAS], 2,6-diaminohexanoeyl β-alanine cholesteryl ester bistrifluoroacetic acid salt [CAL], 2,4-diaminobutyroyl β-alanine cholesteryl ester bistrifluoroacetic acid salt [CAB], N,N-bis(3-aminopropyl)-3-aminopropionyl β-alanine cholesteryl ester tristrifluoroacetic acid salt [CASD], [N,N-bis(2-hydroxyethyl)-2-aminoethyl]aminocarboxy cholesteryl ester [JK-154], carnitine ester lipids, stearyl carnitine ester, myristyl carnitine ester, stearyl stearoyl carnitine ester chloride salt [SSCE], L-stearyl stearoyl carnitine ester [L-SSCE], stearyl oleoyl carnitine ester chloride [SOCE], palmityl palmitoyl carnitine ester chloride [PPCE], myristyl myristoyl carnitine ester chloride [MMCE], L-myristyl myristoyl carnitine ester chloride [L-MMCE].

* * * * *

UNITED STATES PATENT AND TRADEMARK OFFICE
CERTIFICATE OF CORRECTION

PATENT NO. : 5,972,600
DATED : October 26, 1999
INVENTOR(S) : Szoka, Jr. et al.

It is certified that error appears in the above-identified patent and that said Letters Patent is hereby corrected as shown below:

In column 1, line 57, delete "dioctadecyidimethylammonium" and insert therefor --dioctadecyldimethylammonium--.

In column 5, line 33, delete "successful" and insert therefor --successfully--.

In column 5, line 37, delete "step" and insert therefor --steps--.

In column 5, line 39, delete "of" and insert therefor --on--.

In column 7, line 61, delete "dimehtyl" and insert therefor --dimethyl--.

In column 8, line 5, delete "amid'" and insert therefor --amide--.

In column 9, line 63, at the end of the line delete "2H" and insert therefor --2H$^{+}$--.

In column 10, line 7, delete "(2mg)" and insert therefor --(2ml)--.

In column 12, line 22, delete "carriers" and insert therefor --carries--.

In column 12, line 36, delete "separation" and insert therefor --separations--.

In column 14, line 17, delete "dimehtyl" and insert therefor --demethyl--.

Signed and Sealed this

Tenth Day of April, 2001

Attest:

NICHOLAS P. GODICI

Attesting Officer     Acting Director of the United States Patent and Trademark Office